(12) United States Patent
Andrews et al.

(10) Patent No.: US 6,525,325 B1
(45) Date of Patent: Feb. 25, 2003

(54) SYSTEM FOR QUANTIFYING THE HYDROCARBON CONTENT OF AQUEOUS MEDIA

(75) Inventors: John M. Andrews, San Diego, CA (US); Stephen H. Lieberman, La Mesa, CA (US); Lora L. Kear-Padilla, La Mesa, CA (US); Virginia Games, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 53 days.

(21) Appl. No.: 09/814,089

(22) Filed: Mar. 21, 2001

(51) Int. Cl.$^7$ .............................................. G01N 21/64
(52) U.S. Cl. .................... 250/461.1; 250/372; 250/573; 250/574; 250/301
(58) Field of Search ................................ 250/372, 573, 250/574, 461.1, 301; 356/326, 336, 337, 338, 339, 340, 436, 441, 442

(56) References Cited

U.S. PATENT DOCUMENTS

| | | |
|---|---|---|
| 3,917,945 A | 11/1975 | Sema et al. |
| 4,057,721 A | 11/1977 | deVial et al. |
| 4,434,364 A | 2/1984 | Correa et al. |
| 4,446,370 A | 5/1984 | Gergely |
| 4,814,614 A | 3/1989 | Tsui |
| 4,953,978 A * | 9/1990 | Bott et al. .................. 356/336 |
| 5,381,002 A | 1/1995 | Morrow et al. |
| 5,420,432 A * | 5/1995 | Manook et al. ............. 250/373 |
| 5,461,236 A | 10/1995 | Gram et al. |
| 5,489,977 A | 2/1996 | Winslow et al. |
| 5,656,810 A | 8/1997 | Alfano et al. |
| 5,974,860 A | 11/1999 | Kuroda et al. |

FOREIGN PATENT DOCUMENTS

WO  WO 92/02886  2/1992

OTHER PUBLICATIONS

Andrews, J. M. et al., "Neural network approach to qualitative identification of fuels and oils from laser induced fluorescense spectra", *Analytica Chimica Acta*, 285, 1994, pp. 237–246.

* cited by examiner

*Primary Examiner*—Constantine Hannaher
*Assistant Examiner*—Tim Moran
(74) *Attorney, Agent, or Firm*—Peter A. Lipovsky; Jim A. Ward; Mike A. Kagan

(57) ABSTRACT

A system for quantifying the petroleum content of aqueous media includes a sample cell; a first light source for generating a first light signal that stimulates fluorescent emissions when the first light signal irradiates hydrocarbons present in an aqueous solution in the sample cell; a spectral detector for generating a first electrical signal that represents spectral components of the fluorescent emissions in response to detecting the fluorescent emissions that are emitted from the sample cell; a second light source for generating a coherent light signal that is transformed into scattered light signals when the coherent light irradiates oil droplets in the aqueous solution; a detector for generating a second electrical signal in response to detecting scattered light signals emitted from the tube, where the second electrical signal represents the intensities and scatter angles of the scattered light signals; and a processor for determining a particle size distribution of the oil droplets from the second electrical signal and the hydrocarbon content of the aqueous solution from the first electrical signal and the particle size distribution.

9 Claims, 6 Drawing Sheets

| DATA RECORD | SAMPLE | PPM<br>OIL CONTENT (ppm) | VECTORIZED DATA SET ||| 
| | | | FLUORESCENCE |||
| | | | FLUORESCENCE INTENSITY AT 280nm | FLUORESCENCE INTENSITY AT 300nm | FLUORESCENCE INTENSITY AT 320nm |
|---|---|---|---|---|---|
| 1 | DFM | 5 | 35 | 56 | 17 |
| 2 | DFM | 25 | 200 | 312 | 92 |
| 3 | JP5 | 5 | 100 | 20 | 32 |
| 4 | JP5 | 25 | 516 | 101 | 158 |
| 5 | WATER | 0 | 4 | 6 | -2 |

FIG. 3A

| PARTICLE SIZE (FROM SCATTERING DATA) | | | |
|---|---|---|---|
| VOLUME CONCENTRATION 2-5 micron | VOLUME CONCENTRATION 5-10 micron | VOLUME CONCENTRATION 10-20 micron | |
| 2 | 2 | 1 | |
| 11 | 9 | 2 | |
| 1 | 2 | 0 | |
| 4 | 10 | 1 | |
| 1 | 0 | 0 | |

FIG. 3B

SYSTEM FOR QUANTIFYING THE HYDROCARBON CONTENT OF AQUEOUS MEDIA

BACKGROUND OF THE INVENTION

The present invention generally relates to sensors that determine the hydrocarbon content of aqueous liquids, and more particularly to a sensor for quantifying hydrocarbon content in aqueous liquids using both fluorescence spectral emissions and particulate size information derived from detection of optical scattering due to the interaction of oil droplets in the liquid and a coherent light signal.

Many industrial processes utilize an oil-content-monitor (OCM) to provide a real-time on-line measure of the amount of petroleum hydrocarbons present in process water or wastewater streams. Bilge discharge monitoring is a common example of OCM usage. Ships at sea treat bilge water to remove oily contaminants prior to discharging the bilge into the surrounding environment. Environmental regulations specify that bilge water may not be pumped overboard if the oil content exceeds 15 part-per-million (ppm) within the coastal zone, or 100 ppm at sea. Shipboard OCMs provide on-line measurements of the amount of fuel or oil present in the treated bilge water. The ship's crew utilizes this information to make ongoing decisions as to whether the processed bilge may be lawfully discharged or requires further treatment. Examples of other OCM applications include on-line monitoring of: oil well process water discharge, car/aircraft wash facilities, power plant effluent, engine cooling water, desalination plant intake, boiler condensate, storm water runoff, and reclaimed groundwater.

Many existing OCM systems use optical methods to measure oil content. OCM sensors based on ultraviolet (UV) fluorescence, optical scattering, or optical transmission/absorption methods are common. Optical techniques have a "stand-off" advantage over other methods in that direct physical contact with the sample is unnecessary.

Most optically based OCMs are single-channel (zero order) instruments, i.e. they utilize one measured parameter to determine hydrocarbon content. The single parameter these instruments measure may include fluorescence emission at a single wavelength band, or suspended-particle scattering at a single angle, or optical absorption at a single wavelength band, or the ratio of single-angle scattering to single wavelength-band transmission, etc. Instrument calibration is performed by applying a mathematical transformation of the single measured datum in order to relate the raw signal to actual oil content. Single channel instruments offer the benefit of a simple univariate calibration model, e.g. the calibration is typically implemented as a linear function of system response.

Accurate quantification when the hydrocarbon species and matrix are not known a priori is simply not possible with single-channel (univariate calibration) methods. Single-channel (univariate calibration) instruments are adequate for applications where the hydrocarbon analyte, aqueous matrix, and mixing conditions are all well characterized and do not vary over time. However, as single-channel instruments they cannot provide accurate oil content measurements when any of the following conditions exist: a) when the type of hydrocarbon analyte is unknown or changing, b) when the background signal is varying, c) when matrix effects are present (i.e. when the sensitivity of the analyte is dependent upon the presence of other species), or d) when physical factors that effect emulsification, e.g. mechanical stirring, temperature, etc. vary. The inaccuracies are due to the fact that a single data point provides insufficient information to resolve multiple unknown parameters. If the instrumental sensitivity is significantly different for two or more types of petroleum products, for example diesel fuel and lube oil, and both are potentially present in the sample, then a given instrumental response cannot be uniquely associated with a single "overall" oil content. Single-channel instruments are also incapable of distinguishing between a signal arising from target analytes and background interference. Signal changes brought about by spectral or physical interferences, common in many applications, cannot be differentiated from signal changes arising from a change in oil content. In a dynamic environment, this leads to erroneous determinations of oil content.

Accurate measurement of small quantities of oil in water (e.g. low mg $L^{-1}$) is extremely difficult when the hydrocarbon type and/or matrix is changing or when physical and chemical interferences are present. Because of the many parameters involved, consistently accurate measurement requires a multi-channel (multivariate measurement and calibration) approach. Multichannel fluorescence and multichannel light scattering can both be used to for real-time measurement of oil content in water. Each method has distinct advantages and disadvantages.

The fluorescence based methods detect the intensity of fluorescence emission from both dissolved and emulsified aromatic hydrocarbons (AHs) when irradiated with ultraviolet light. For a given sample, the wavelength dependent fluorescence emission generally varies with the specific wavelength band used to excite the sample. Excitation frequencies are usually in the 250–350 nm range. More than one excitation wavelength band may be used either simultaneously or in succession to generate multidimensional fluorescence emission spectra.

One of the attractive features of fluorescence is that it provides a very sensitive means of quantifying low levels of dissolved phase petroleum hydrocarbons (aromatics) in water. The aromatic constituents of petroleum, for example, benzene, naphthalene, and their derivatives, are many times more soluble in water than the non-aromatic components, and therefore constitute the bulk of the dissolved phase hydrocarbons in an aqueous mixture.

The response of a given fluorescence based OCM can vary significantly with the specific type of petroleum hydrocarbon analyte as well as with the size of emulsified oil droplets in the sample. The oil-type-dependent response is due to the fact that petroleum products have varying AH content as well as other varying constituents that may quench or absorb AH fluorescence. The AH dependent fluorescence response may vary with the crude or refined product type, (gasoline, lube oil, diesel fuel, jet fuel, etc), origin of crude stock, refining process, etc. In addition, the fluorescence response of oil-in-water emulsions also varies significantly with the size of the emulsified oil droplets. The dependence on droplet size can be complex. For a given oil (in water) volume, as the average droplet volume decreases the total number of droplets and total cross-sectional area increases potentially leading to higher fluorescence yield. However, changing droplet size may also affect solution equilibria and the partitioning of aromatic species into and out of solution. Hence the fluorescence response may increase at some wavelengths and decrease at others.

The light scattering methods generally measure 1) the attenuation of the intensity of light passing through a sample and/or 2) the light scattered by the sample at one or more angles. The scattering is due to the presence of emulsified droplets of oil in the sample. Multi-angle scattering can be used to estimate droplet (or particle) size distribution given in terms of droplet number per size-range, or volume concentration per size range. An advantage of scattering methods is that, unlike fluorescence that targets aromatic hydrocarbons exclusively, they are generally responsive to all types emulsified oils. A severe shortcoming, however, is that scattering cannot detect the dissolved phase of oil constituents. Scattering also poses difficulties in distinguishing between oil droplets and solid particles. Multi-angle scattering and re-emulsification methods help in distinguishing oil droplets from solid particles, but complete compensation for solids content is difficult.

The major technical challenge of OCM design is to maintain quantitative accuracy for online measuring of oil-in-water concentrations in the presence of unknown chemicals and physical interferences, including fluorescent organic compounds, detergents, suspended solid particles, and dissolved salts. Existing instruments and methods for calibrating their response are not appropriate for complex systems. Therefore, a need exists for a reliable and accurate method for determining the concentration of oil droplets in aqueous media.

SUMMARY OF THE INVENTION

The present invention provides an oil content monitor (OCM) that combines the use of multichannel fluorescence and droplet size information to quantify oil contamination of an aqueous media. Fluorescence emission intensity is measured at multiple wavelengths. The intensity at a given wavelength is a function of oil content. The relative intensity differences at different wavelengths are a function of the analyte itself, and can be used to determine which species or class of oil is present. The oil droplet size distribution and oil volume concentration is estimated from optical scattering measurements made at multiple small angles. The invention includes a sample cell; a first light source for generating a first light signal that stimulates fluorescent emissions when the first light signal irradiates hydrocarbons present in an aqueous solution in the sample cell; a spectral detector for generating a first electrical signal that represents spectral components of the fluorescent emissions in response to detecting the fluorescent emissions that are emitted from the sample cell; a second light source for generating a coherent light signal that is transformed into scattered light signals when the coherent light irradiates oil droplets in the aqueous solution; a detector for generating a second electrical signal in response to detecting scattered light signals emitted from the sample cell, where the second electrical signal represents the intensities and scatter angles of the scattered light signals; and a processor for determining a particle size distribution of the oil droplets from the second electrical signal and the hydrocarbon content of the aqueous solution from the first electrical signal and the particle size distribution.

Another embodiment of the invention uses a single optical energy source and includes a sample cell. A light source generates a coherent ultraviolet light signal that stimulates fluorescent emissions when the first light signal irradiates hydrocarbons present in an aqueous sample in the sample cell, where the coherent ultraviolet light signal is transformed into scattered light signals when the coherent ultraviolet light irradiates oil droplets in the aqueous sample. A spectral detector generates a first electrical signal that represents spectral components of the fluorescent emissions in response to detecting the fluorescent emissions that are emitted from the sample cell. The spectral detector also generates a second electrical signal in response to detecting scattered light signals emitted from the tube, where the second electrical signal represents the intensities and scatter angles of the scattered light signals. A processor determines a particle size distribution of the oil droplets from the second electrical signal and estimates the hydrocarbon concentration content of the aqueous sample from the first electrical signal and the particle size distribution.

An important advantage of the invention is that it employs both the spectral components of fluorescent emissions generated by irradiating the aqueous test sample with ultraviolet light, and the particle size distribution of oil particles suspended in the aqueous test sample in order to determine the oil content of the aqueous test sample.

Other advantages of the invention will become more apparent upon review of the accompanying drawings and specification, including the claims.

BRIEF DESCRIPTION OF THE DRAWINGS

FIG. 3 is an example of a data vector that associates levels of hydrocarbon contamination to actual spectral and particulate size data for several liquid test samples.

Throughout the several views, like elements are referenced using like references.

DESCRIPTION OF THE PREFERRED EMBODIMENT

Figure 1:
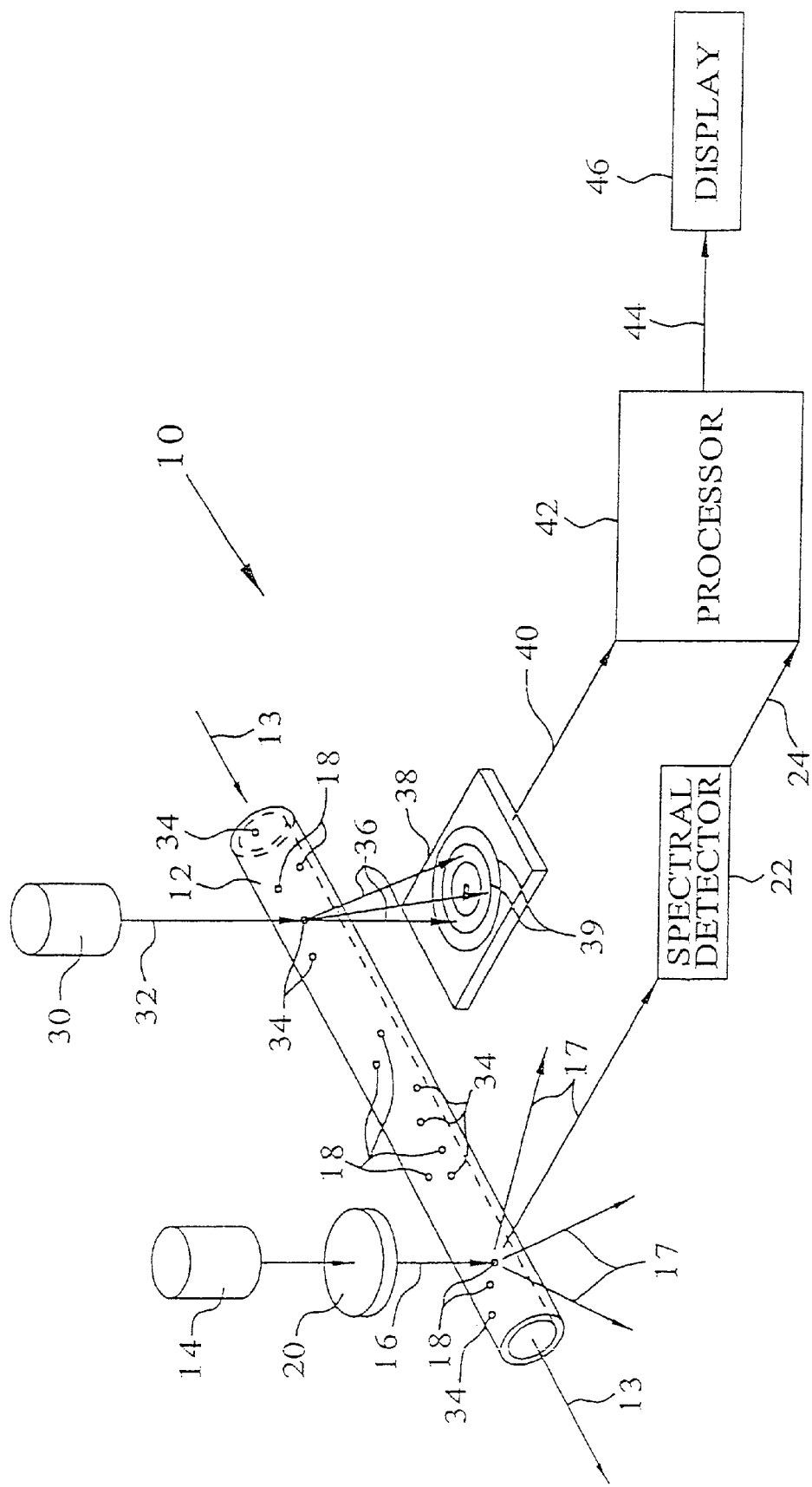
FIG. 1 shows a system for quantifying the petroleum content of aqueous media that embodies features of the present invention.

The present invention is directed to a system for quantifying the hydrocarbon content of aqueous media. Referring to FIG. 1, system 10 includes a sample cell 12, which may be implemented as a transparent tube, in which is present an aqueous sample 13. The sample cell 12 may be made of a transparent material such as quartz or glass that is generally chemically inert to hydrocarbons. The sample cell 12 may also be implemented in aluminum, Teflon®, or stainless steel and have transparent windows, not shown, for allowing the penetration and emission of light between the interior and exterior of the cell. A light source 14 generates a light signal 16 having ultraviolet components. Light signal 16 is directed into sample cell 12 to stimulate fluorescent emissions 17 from any hydrocarbons 18 that may be present in the aqueous sample 13 that are irradiated by light signal 16. Light source 14 may be economically implemented as a broadband light source, such as a xenon flashlamp, in which case light signal 16 is a broadband light beam having multi-spectral, including ultraviolet, components. An optical filter or monochrometer 20 may be used to limit the spectral bandpass of light signal 16. However, light source 16 may also be implemented using any UV source such as a deuterium lamp, light emitting diode, or laser. Multiple light sources as well as multiple excitation energies could be used to enhance selectivity. In response to detecting fluorescent emissions 17, a spectral detector 22 generates electrical signals 24 that represent one or more spectral components of signal 17 having different wavelengths for characterizing fluorescent emissions 17. Spectral detector 22 may be implemented as a spectrograph (or monochrometer or optical filter array) coupled photodiode, photodiode array, CCD, photomultiplier tube (PMT), or multianode PMT. In the preferred embodiment, the field of view 23 of the spectral detector 22 is oriented so that the path of light signal 16 does not excite the spectral detector 22. For example, the path of light signal 16 may be orthogonal to a vector that is normal to light sensing surface of detector 22.

System 10 relies on multi-angle optical scattering techniques for determining the size-distribution of droplets 34 in aqueous test sample 13. Droplets 34 may be emulsified oil droplets in aqueous test sample 13. Analysis of the sizes of droplets 34 is achieved by measuring the intensity of scattered light signals at many (32) angles, as for example, between 0.1 and 20 degrees. Coherent light source 30 generates a coherent light signal 32 that is directed into sample cell 12. If light signal 32 irradiates any emulsified oil droplets 34 that may be suspended in aqueous test sample 13, the interaction between the light signal 32 and the droplets or particles 34 causes the light signal 32 to become divided into scattered light signals 36. Scattering refers to the transformation of coherent light signal 32 into many light signals 36 that propagate at an angle with respect to the direction of coherent light signal 32. Scattered light signals 36 are detected by multi-angle photodetector 38, such as a ring detector, charge couple device (CCD), or photodiode array, from which is determined the intensity and angle of scatter for each detected scattered light signal 36 with respect to the direction of coherent light signal 32. The multi-angle photodetector 38 generates electrical signals, collectively referenced as signal 40 from locations on the photodetector 38 where the scattered light signals 36 irradiate light detecting elements 39. Signal 40 represents the intensities and scatter angles of light signals 36 that are detected by light scattering detector 38. Software executed in processor 42 employs the information encoded in signal 40 to determine the size distribution of oil droplets 34 in aqueous test sample 13 using well known techniques. Software for determining particle size distribution from optical intensities and scatter angles of light passing through a liquid is available from Sequoia Scientific, Inc.

Processor 42 implements a calibration algorithm that uses the particle size distribution of oil droplets 34 previously determined by processor 42 using intensity and scatter angle information encoded in signal 40, and the spectral component information from flourescent emissions 17 represented in signals 24 to determine a value representing the hydrocarbon concentration content $H_c$ of hydrocarbons 34 present in the aqueous test sample 13. Implementation of the algorithm by processor 42 results in the generation of an output signal 44 representing the hydrocarbon concentration content $H_c$ of oil in test sample 34 that is provided to display 46. Display 46 presents $H_c$ in human readable form, as for example, "Oil content=25 ppm." By way of example, display 46 may be implemented as a video monitor, a printer, a strip chart recorder, and the like.

The development of the calibration algorithm is described with reference to FIG. 2. First, the types of fluids, degrees of contamination, and matrix conditions are established for a particular monitoring application at step 50. FIG. 3 illustrates a table of example data for various mixtures and types of fluids that have predetermined levels of hydrocarbon contamination and particle size contamination that encompass the scope of the levels of contamination of test samples 13 likely to be examined by sensor 10. For example, the range of hydrocarbon contamination, typically measured in parts per million (ppm), in test sample 13 may range from 0 parts per million (ppm) to 25 ppm, and the size-distribution particles 34 may range from 0 to 20 microns.

Next, at step 52, various test samples 13 (which may include a water and/or sea water matrix) having different types and levels of hydrocarbon contamination and particle size distributions that span the defined scope of such characteristics are formulated. For example, data record number one of the data set shown in FIG. 3 represents a sample mixture of sea water contaminated with 5 ppm of marine diesel fuel (DFM). Data record numbers 3 and 4 represent mixtures of sea water contaminated with jet fuel (JP5). Data record number 1 is characterized by spectra data, i.e., fluorescent emission intensity at different wavelengths, and the volume concentrations or size distributions of oil droplets 34. More specifically, data record number one represents an actual sample of seawater contaminated with 5 parts per million (ppm) of DFM. Measured fluorescent relative intensities for sample 1 at 280 nm, 300 nm, and 320 nm are 35, 56, and 17, respectively. For purposes of explaining the invention, FIG. 3 shows 5 data records associated with 5 different test samples of contaminated water or sea water that are used to derive the calibration algorithm. Fluorescent data generated by each aqueous sample 13 is used to construct data records such as the ones shown in FIG. 3. However, the actual development of the calibration algorithm may employ any suitable number of data records, the number of which may be much greater than five. In general, the calibration algorithm will more accurately relate spectral characteristics and particle sizes to values of hydrocarbon contamination when hundreds, and even thousands of data records are used to derive the algorithm. In addition, each data record may contain many more fluorescence intensity values than the three shown, as well as a greater number of volume concentrations (i.e., size distributions) than as shown in FIG. 3.

At step 54, raw data such as shown in FIG. 3 is converted to a more usable form through normalization, scaling, and/or mean centering to create more robust calibration models for development of the calibration algorithm. At step 56, the data shown in FIG. 2 is divided into three independent groupings. One data record is used to train or develop the calibration algorithm, the second set is used during the training process to test the algorithm, and the third set is used to validate the calibration algorithm. The derivation of the calibration algorithm assumes that the hydrocarbon concentration content $H_c$ of aqueous sample 13 is a function of the spectral components of fluorescent emissions 17 and particle size distribution of oil droplets 34. It is to be noted that particle size distribution may be derived using standard techniques such as optical scattering or image analysis.

Figure 2:
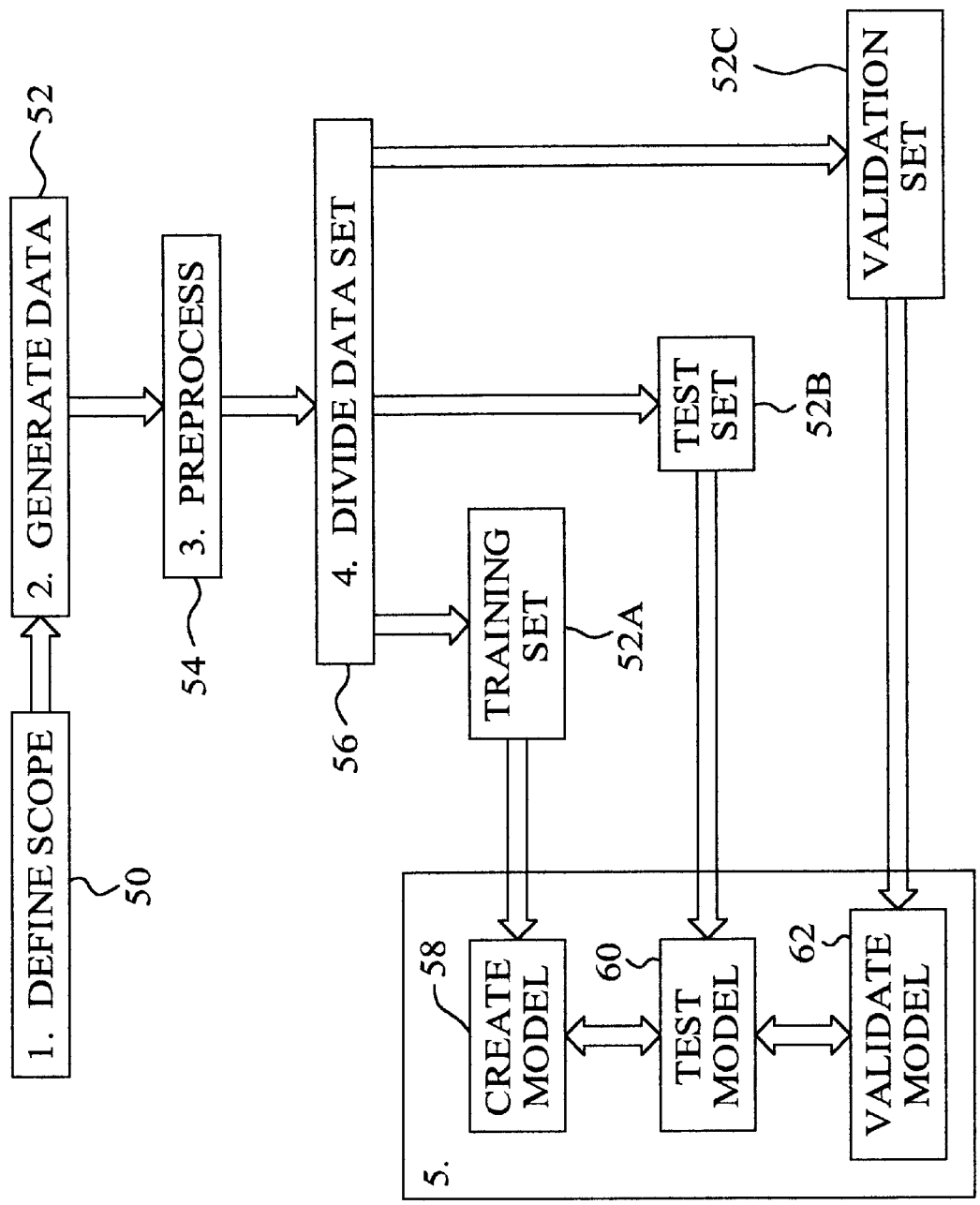
FIG. 2 illustrates the process of developing an algorithm for transforming sample data into a value representing hydrocarbon contamination.

Next at step 58 shown in FIG. 2, the calibration algorithm is derived. There are many mathematical techniques suitable for developing the calibration algorithm. Examples of suitable techniques include multiple linear regression, multiple nonlinear regression, principle components regression, partial least squares regression, and recursive least squares regression. The preferred method for developing the calibration algorithm includes the use of artificial neural networks. Artificial neural networks, such as back propagation, provide a convenient and powerful means of fusing multivariate, generally nonlinear, spectral and droplet size data, such as found in the data vector presented by way of example in FIG. 3, and transforming the data into an oil content value. Still other methods include using a look-up table, or a nearest-neighbor classifier.

The calibration algorithm may be developed using a three layer back-propagation neural network (BPNN) using NeuralWorks Professional II Plus by NeuralWare, Inc.and a Pentium II 450-MHz PC with 128 MB-RAM. Although the calibration algorithm was developed using a three-layer back-propagation neural network, it is to be understood that other types of neural networks may also be used. By way of example, the BPNN may include input, hidden, and output layers. The output layer of the BPNN has a single node (neuron) corresponding to oil content in parts per million (ppm). The input layer has a single node for each of the input values that comprise each data record in the data vector as shown in FIG. 3. For example, in FIG. 3, each data record includes three fluorescent emission data and three volume concentrations for three droplet size ranges. Thus, using the example of the data vector in FIG. 3, BPNN has six input nodes (neurons) corresponding to the fluorescence intensities at three different wavelengths and the volume concentrations for three droplet size ranges for each data record. Although not shown, the input layer may also include additional nodes or neurons for optical transmission and the scattering intensity at the same angle as the fluorescent detection for each data record. The BPNN transfer function used by each node is preferably a sigmoid or hyperbolic tangent, although other functions may also be used. The optimal number of nodes in the hidden layer is determined during the training process by trial and error and by iterative improvement, as for example, by trying different numbers of nodes in the hidden layers until the user is satisfied with the results. Seven hidden layers were found to provide satisfactory results for the present invention. The data set in FIG. 3 is split into a training set, a test set, and a validation set, as exemplified in FIG. 2. The BPNN is trained using standard, well known methodology for adjusting weight parameters ultimately selected for the final version of the calibration algorithm.

Once the weights are determined so that BPNN provides satisfactory results, the BPNN is considered to be "trained," whereupon the calibration algorithm then is defined as a sequence of mathematical functions that employ the weights developed by the BPNN generally as coefficients. Satisfactory results are defined where the absolute value of the difference between the calculated value of $H_{c\text{-}calc}$ and the actual value of $H_c$ for a particular data record is less than some acceptable limit $\delta$, i.e., $|H_{c\text{-}calc} - H_c| \leq \delta$, where $H_{c\text{-}calc}$ represents the calculated hydrocarbon concentration content of aqueous sample 13 that is determined by the calibration algorithm. The calibration algorithm is characterized as a multivariate calibration algorithm because it employs multiple data inputs, as for example six inputs from each data record of FIG. 3, in order to determine the level of contamination of test sample 13. However, it is to be understood that the calibration algorithm may employ any number of data inputs as required to suit the requirements of a particular application. The algorithm may be implemented in software for execution by processor 42, or may alternatively be implemented in hardware if faster performance is desired.

Once the calibration algorithm has been successfully tested, then the third data set may be inserted into the algorithm to validate the algorithm, and thereby provide a separate, independent check of the validity of the algorithm. The difference between testing and validation data is that validation data is not used to develop the model. If a calibration model does not perform to the desired degree of accuracy with the validation set, then the model is improved using the training and test data records. After being validated, the calibration algorithm may be implemented in processor 42 for processing data.

In the operation of sensor 10, data signals 24 and 40 are input into processor 42 whereupon processor 42 determines the particle size distribution of oil droplets in aqueous sample 13 from information encoded in signal 40. Then, the calibration algorithm is executed by processor 42 to calculate $H_{c\text{-}calc}$ which estimates the actual hydrocarbon concentration content $H_c$ in aqueous sample 13 from spectral data of fluorescent emissions 17 encoded in signal 24 and the particle size distributions. Processor 42 generates an output signal 44 that represents $H_{c\text{-}calc}$ which is provided to display 46. Then display 46 presents the calculated level of hydrocarbon concentration content $H_{calc}$ in human readable form, such as in a textual and/or alpha/numeric format.

In practice, sensor 10 may be placed so that the aqueous sample 13 flows through the sample cell 12. For example, for bilge monitoring applications the sample stream 13 is typically the aqueous effluent of an oil-water separator. The user determines the data acquisition rate, i.e. the number of measurements per unit time. The detection of light signals 17 and 36 and processing of signals 24 and 40 may be performed by processor 42 on a time scale of a few seconds or less, whereupon the presentation of display 46 is updated after each measurement.

Figure 4:
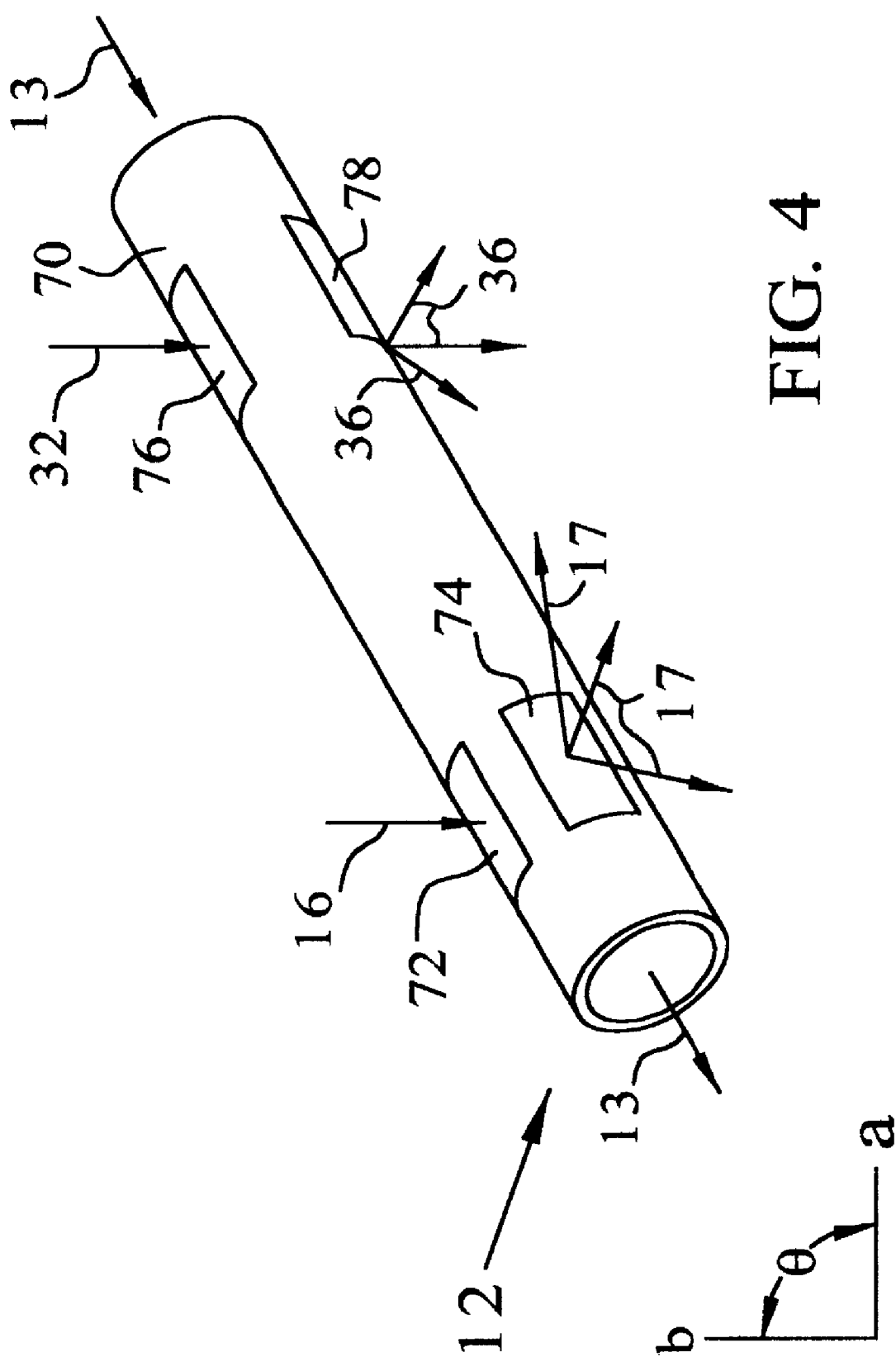
FIG. 4 shows a second embodiment of the sample cell.

In another embodiment of the invention, shown in FIG. 4, sample cell 12 may be implemented as a tube 70 in which are mounted windows 72, 74, 76, and 78, which may be made of quartz or glass. Fluorescent excitation light signal 16 enters window 72 and if any hydrocarbons that are present in test sample 13 are irradiated by light signal 16, the fluorescent light signals 17 will be emitted out of tube 70 through window 74 for detection by spectral detector 22. Windows 72 and 74 are preferably offset radially by an angle θ, such as 90° with respect to reference axes a and b so that the propagation direction of fluorescent excitation light signal 16 does not transect both windows 72 and 74 in order to prevent light signal 16 from entering the field of view of spectral detector 22. Coherent light signal 32 enters window 76 and if signal 32 irradiates any emulsified oil droplets 34, light signal 32 is transformed into scattered light signals 37 which are emitted from tube 70 through window 78. Windows 76 and 78 may preferably be mounted diametrically opposed to each other in tube 70 as shown in FIG. 4, however, such a configuration is not necessary. Tube 70 may be made of stainless steel because stainless steel has excellent chemical resistance to the types of contaminants likely to be found in test sample 13.

Figure 5:
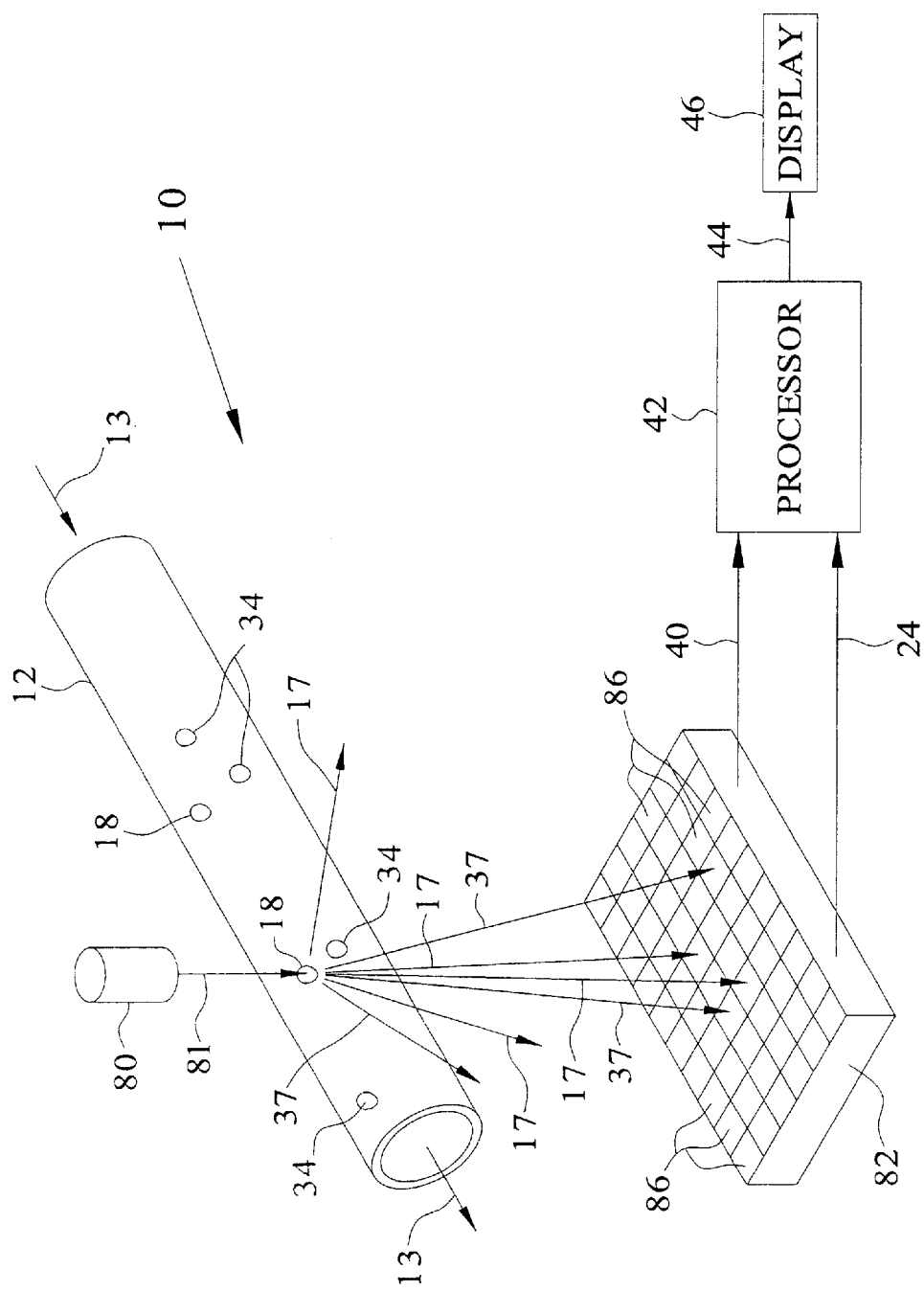
FIG. 5 shows an embodiment of the present invention that includes a single excitation optical energy source.

FIG. 5 illustrates another embodiment of system 10 which includes sample cell 12 through which flows aqueous sample 13. An ultraviolet coherent light source 80 generates an ultraviolet coherent light signal 81 that is directed into sample cell 12. UV light signal 81 stimulates fluorescent emissions 17 from any hydrocarbons 18 that may be present in the aqueous sample 13 that are irradiated by light signal 81. Spectral photo detector 82, such as a CCD array having optical sensing elements 86, detects fluorescent emissions 17 and the intensities and locations where scatter light signals 37 irradiate photo detector 82. Scatter light signals 37 are produced as a result of UV light signal 81 irradiating particular oil droplets 36 in aqueous sample 13. Photo detector 82 generates a signal 24 that represents selected spectral characteristics of fluorescent emissions 17. In the embodiment of sensor 10 shown in FIG. 5, the field of view of photo detector 82 may detect UV light signal 81. The effect of signal 81 irradiating photo detector 82 may be nulled because the optical sensing elements 86 that are irradiated by UV signal 81 may be taken off-line or by appropriate use of algorithms executed in processor 42.

Photodetector 82 generates electrical signals, collectively referenced as signal 40 from locations on the photodetector 82 where the scattered light signals 37 irradiate light detecting elements 86 of photo detector 82. Signal 40 represents the intensities and scatter angles of light signals 37 that are detected by photo detector 82. Software executed in processor 42 employs the information encoded in signal 40 to determine the size distribution of oil droplets 34 in aqueous test sample 13 using well known techniques. Because photo detector 82 detects both fluorescent emissions 17 and scattered light signals 37, only one optical energy source is required.

Processor 42 implements an algorithm that uses the particle size distribution of oil droplets 34 previously determined by processor 42 using intensity and scatter angle information encoded in signal 40, and the spectral component information from flourescent emissions 17 represented in signal 24 to determine a value $H_{c\text{-}calc}$ representing the hydrocarbon concentration content $H_c$ of hydrocarbons 34 present in the aqueous test sample 13. Implementation of this algorithm by processor 42 results in the generation of an output signal 44 representing the hydrocarbon concentration content $H_{c\text{-}calc}$ of oil in test sample 34 that is provided to display 46. Display 46 presents $H_{c\text{-}calc}$ in human readable form, as for example, "Oil content=25 ppm."

In another embodiment of sensor 10, raw data encoded in signal 40, which represents intensity and location data corresponding to the locations on detector 38 that are irradiated by scattered light signals 37, may be directly input into the BPNN to develop the calibration algorithm in lieu of using the particle size distribution data as inputs into the BPNN. Therefore, processor 42 may execute the algorithm to determine the hydrocarbon content $H_{c\text{-}calc}$ of aqueous test sample 13 directly from information encoded in signals 24 and 40, without having to determine the particle size distribution of particles 34. In this embodiment, the calibration algorithm estimates the hydrocarbon content $H_{calc}$ based on the fluorescent emissions 17 and the scattering light signals 37, and does not employ the particle size distribution to estimate $H_{c\text{-}calc}$ Obviously, many modifications and variations of the present invention are possible in light of the above teachings. For example, particle size distributions may also be determined based on optical imaging and other techniques. It is therefore to be understood that within the scope of the appended claims, the invention may be practiced otherwise than as specifically described.

We claim:

1. A system for quantifying the hydrocarbon concentration content of an aqueous media, comprising:
   a sample cell;
   a first light source for generating a first light signal that stimulates fluorescent emissions when said first light signal irradiates hydrocarbons present in an aqueous sample in said sample cell;
   a spectral detector for generating a first electrical signal that represents spectral components of said fluorescent emissions in response to detecting said fluorescent emissions emitted from said sample cell;
   a second light source for generating a coherent light signal that is transformed into scattered light signals when said coherent light irradiates oil droplets in said aqueous sample;
   a detector for generating a second electrical signal in response to detecting scattered light signals emitted from said sample cell, where said second electrical signal represents the intensities and scatter angles of said scattered light signals; and
   a processor for determining a) a particle size distribution of said oil droplets from said second electrical signal; and b) the hydrocarbon concentration content of said aqueous sample from said first electrical signal and said particle size distribution.

2. The system of claim 1 wherein said sample cell is a tube.

3. The system of claim 1 wherein said processor executes a multivariate calibration algorithm for determining said hydrocarbon concentration content of said aqueous sample.

4. The system of claim 1 wherein said first light signal is an ultraviolet light signal.

5. A system for quantifying the petroleum concentration content of aqueous media, comprising:
   a sample cell;
   a light source for generating a coherent ultraviolet light signal that stimulates fluorescent emissions when said first light signal irradiates hydrocarbons present in an aqueous sample in said sample cell, where said coherent ultraviolet light signal is transformed into scattered light signals when said coherent ultraviolet light signal irradiates oil droplets in said aqueous sample;
   a spectral detector for generating a first electrical signal that represents spectral components of said fluorescent emissions in response to detecting said fluorescent emissions that are emitted from said sample cell, and for generating a second electrical signal in response to detecting scattered light signals emitted from said tube, where said second electrical signal represents the intensities and scatter angles of said scattered light signals; and
   a processor for determining a particle size distribution of said oil droplets from said second electrical signal and the hydrocarbon concentration content of said aqueous sample from said first electrical signal and said particle size distribution.

6. The system of claim 5 where in said sample cell is a tube.

7. The system of claim 5 wherein said processor executes a multivariate calibration algorithm for determining said hydrocarbon concentration content of said aqueous sample.

8. A system for quantifying the hydrocarbon concentration content of an aqueous media, comprising:
   a sample cell;
   a first light source for generating a first light signal that stimulates fluorescent emissions when said first light signal irradiates hydrocarbons present in an aqueous sample in said sample cell;
   a spectral detector for generating a first electrical signal that represents spectral components of said fluorescent emissions in response to detecting said fluorescent emissions emitted from said sample cell;
   a second light source for generating a coherent light signal that is transformed into scattered light signals when said coherent light irradiates oil droplets in said aqueous sample;
   a detector for generating a second electrical signal in response to detecting scattered light signals emitted from said sample cell, where said second electrical signal represents the intensities and scatter angles of said scattered light signals; and
   a processor for determining the hydrocarbon concentration content of said aqueous sample from said first and second electrical signals.

9. A system for quantifying the petroleum concentration content of aqueous media, comprising:

a sample cell;

a light source for generating a coherent ultraviolet light signal that stimulates fluorescent emissions when said coherent ultraviolet light signal irradiates hydrocarbons present in an aqueous sample in said sample cell, where said coherent ultraviolet light signal is transformed into scattered light signals when said coherent ultraviolet light irradiates oil droplets in said aqueous sample;

a spectral detector for generating a first electrical signal that represents spectral components of said fluorescent emissions in response to detecting said fluorescent emissions that are emitted from said sample cell, and for generating a second electrical signal in response to detecting scattered light signals emitted from said tube, where said second electrical signal represents the intensities and scatter angles of said scattered light signals; and a processor for determining the hydrocarbon concentration content of said aqueous sample from said first and second electrical signals.

* * * * *